US012742151B2

(12) United States Patent
Yumoto et al.

(10) Patent No.: US 12,742,151 B2
(45) Date of Patent: Sep. 22, 2026

(54) PRODUCTION METHOD FOR MICROGLIA

(71) Applicants: Masayuki Yumoto, Kanagawa (JP); Yudai Kawashima, Kanagawa (JP); Hikaru Watanabe, Kanagawa (JP); Toshihiko Hosoya, Tokyo (JP); Minoru Ko, Tokyo (JP)

(72) Inventors: Masayuki Yumoto, Kanagawa (JP); Yudai Kawashima, Kanagawa (JP); Hikaru Watanabe, Kanagawa (JP); Toshihiko Hosoya, Tokyo (JP); Minoru Ko, Tokyo (JP)

(73) Assignees: Ricoh Company, Ltd., Tokyo (JP); Elixirgen Scientific, Inc., Baltimore, MD (US)

( * ) Notice: Subject to any disclaimer, the term of this patent is extended or adjusted under 35 U.S.C. 154(b) by 647 days.

(21) Appl. No.: 18/176,959

(22) Filed: Mar. 1, 2023

(65) Prior Publication Data

US 2023/0323295 A1 Oct. 12, 2023

(30) Foreign Application Priority Data

Mar. 22, 2022 (JP) ................................ 2022-046010

(51) Int. Cl.
*C12N 5/079* (2010.01)

(52) U.S. Cl.
CPC ........ *C12N 5/0622* (2013.01); *C12N 2501/60* (2013.01); *C12N 2506/45* (2013.01)

(58) Field of Classification Search
CPC .............. C12N 5/0622; C12N 2501/60; C12N 2506/45
See application file for complete search history.

(56) References Cited

U.S. PATENT DOCUMENTS

| | | | |
|---|---|---|---|
| 6,943,016 | B1 | 9/2005 | Ridet et al. |
| 2020/0063105 | A1 | 2/2020 | Ng et al. |
| 2021/0277345 | A1 | 9/2021 | Aratani et al. |

FOREIGN PATENT DOCUMENTS

| | | |
|---|---|---|
| JP | 2003-524391 | 8/2003 |
| JP | 2021-136998 | 9/2021 |
| WO | 2020/239807 | 12/2020 |
| WO | 2020/252477 | 12/2020 |

OTHER PUBLICATIONS

Chen et al., "Efficient Conversion of Human Induced Pluripotent Stem Cells into Microglia by Defined Transcription Factors", Stem Cells Report, vol. 16, May 11, 2021, pp. 1363-1380.
Dräger et al., "A CRISPRi/a platform in human iPSC-derived microglia uncovers regulators of disease states", Nature Neuroscience, vol. 25, Sep. 2022, pp. 1149-1162.
Extended Search Report received for European Patent Application No. 23159583.6, mailed on Aug. 16, 2023, 7 pages.
Pocock et al., "Modelling microglial function with induced pluripotent stem cells: an update", Nature Reviews, Neuroscience, vol. 19, Aug. 2018, pp. 445-452.
Sonn et al., "Single transcription factor efficiently leads human induced pluripotent stem cells to functional microglia", Inflammation and Regeneration, vol. 42, No. 20, 2022, pp. 1-20.
Wong et al., "Direct Conversion of Human-Induced Pluripotent Stem Cells into Functional Microglia-Like Cells by Defined Transcription Factors", Poster Presentations, P4-478, Jul. 17, 2019, p. S1495-S1496.

*Primary Examiner* — Peter Paras, Jr.
*Assistant Examiner* — Gillian C. Reglas
(74) *Attorney, Agent, or Firm* — Grüneberg Global IP, PLLC

(57) ABSTRACT

There is provided a production method for microglia, including a step of introducing, into pluripotent stem cells, a nucleic acid including an open reading frame of a transcription factor that increases expression of a Complement C3 (C3) gene. In the production method, the transcription factor is selected from the group consisting of SPI1, CEBPA, PTAFR, FLI1, MEF2C, EGR2, RUNX1, TNF, CEBPB, IKZF1, KLF6, NFIC, ELF4, PAX8, PRDM1, MEF2A, and NR4A3.

2 Claims, 7 Drawing Sheets

PRODUCTION METHOD FOR MICROGLIA

BACKGROUND OF THE INVENTION

Field of the Invention

The present invention relates to a production method for microglia. Priority is claimed on Japanese Patent Application No. 2022-046010, filed Mar. 22, 2022, the content of which is incorporated herein by reference.

Description of Related Art

Cells of the central nervous system are difficult to obtain. On the other hand, various cells including cells of the central nervous system cells have become available by differentiating pluripotent stem cells such as induced pluripotent stem cells (iPSC) into cells of interest. Further, disease model cells can also be produced by differentiating pluripotent stem cells derived from a patient into cells of interest.

Microglia are one kind of glial cells of the central nervous system. Glial cells are a general term for cells that are not nerve cells that constitute the nervous system. Microglia are known as central immunocompetent cells. Unlike cells of the central nervous system, microglia are conceived to be derived from the mesoderm and play a role as immune cells in the brain. At the time in a disease state, microglia become activated, which involves cell body hypertrophy and cell proliferation. It is known that activated microglia change the expression of various molecules including receptors in the cell membrane, migrate to a lesion part, phagocytize damaged cells or extracellular proteins such as amyloid β protein, and produce humoral factors (an inflammatory factor, a cytotoxic factor, a nutritional factor, and the like). Microglia play a major role in the mechanisms of central nervous system diseases and thus have been suggested to be associated with Alzheimer's disease.

SUMMARY OF THE INVENTION

However, a conventional method of producing microglia from pluripotent stem cells requires 30 or more days of culture in order to obtain microglia. Accordingly, an object of the present invention is to provide a technique for producing microglia from pluripotent stem cells in a short period of time.

A production method for microglia according to the present invention includes a step of introducing, into pluripotent stem cells, a nucleic acid including an open reading frame of a transcription factor that increases expression of a Complement C3 (C3) gene.

According to the present invention, it is possible to provide a technique for producing microglia from pluripotent stem cells in a short period of time.

DETAILED DESCRIPTION OF THE INVENTION

[Production Method for Microglia]

Figure 1:
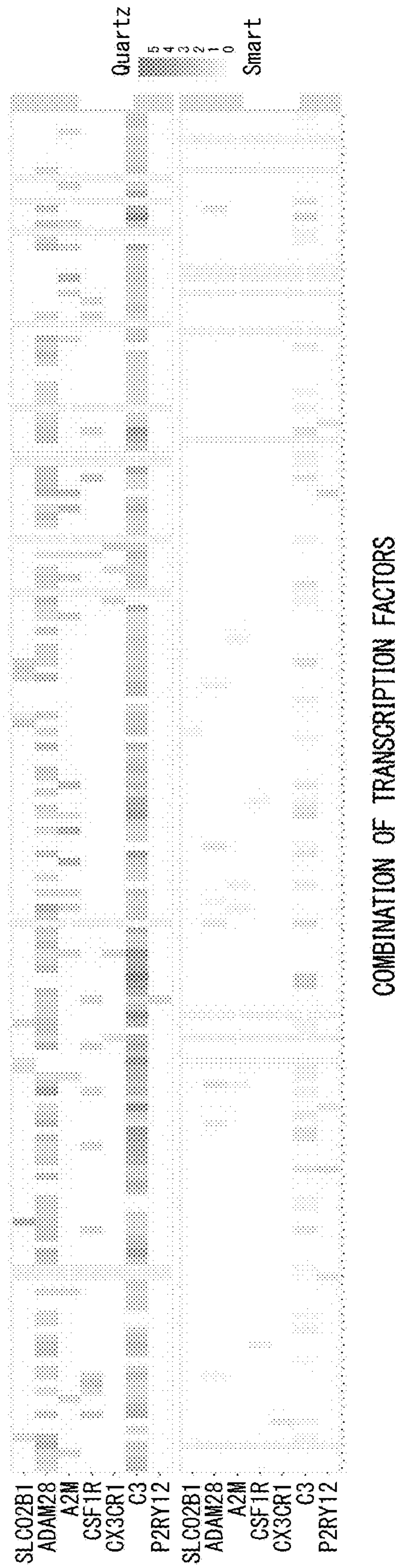
FIG. 1 is a heat map showing the expression state of microglial marker genes in Experimental Example 3.

In one embodiment, the present invention provides a production method for microglia, which includes a step of introducing, into pluripotent stem cells, a nucleic acid including an open reading frame of a transcription factor that increases expression of a Complement C3 (C3) gene.

As will be described later in Examples, the inventors of the present invention revealed that the production of microglia, which conventionally takes 30 days or longer, can be carried out within 14 days by the production method of the present embodiment. In addition, as will be described later in Examples, the microglia produced by the production method of the present embodiment have phagocytic activity and thus have a function of microglia.

In microglia, microglial marker genes are expressed, and a function of microglia, such as phagocytic activity, is exhibited. Examples of the microglial marker gene include Purinergic Receptor P2Y12 (P2RY12), Complement C3 (C3), C-X3-C Motif Chemokine Receptor 1 (CX3CR1), Colony Stimulating Factor 1 Receptor (CSF1R), Alpha-2-Macroglobulin (A2M), ADAM Metallopeptidase Domain 28 (ADAM28), Plexin Domain Containing 2 (PLXDC2), Lysosomal Protein Transmembrane 5 (LAPTM5), Solute Carrier Organic Anion Transporter Family Member 2B1 (SLCO2B1), and Lymphocyte Antigen 86 (LY86), which will be described later in Examples.

The NCBI accession number of the nucleotide sequence of cDNA of the human P2RY12 gene is NM_022788.5, NM_176876.3, or the like. The NCBI accession number of the nucleotide sequence of cDNA of the human C3 gene is NM_000064.4. The NCBI accession number of the nucleotide sequence of cDNA of the human CX3CR1 gene is NM_001171171.2, NM_001171172.2, NM_001171174.1, or the like. The NCBI accession number of the nucleotide sequence of cDNA of the human CSF1R gene is NM_001288705.3, NM_001349736.2, NM_001375320.1, or the like. The NCBI accession number of the nucleotide sequence of cDNA of the human A2M gene is NM_000014.6, NM_001347423.2, NM_001347424.2, or the like. The NCBI accession number of the nucleotide sequence of cDNA of the human ADAM28 gene is NM_001304351.2, NM_014265.6, NM_021777.5, or the like. The NCBI accession number of the nucleotide sequence of cDNA of the human PLXDC2 gene is NM_001282736.2, NM_032812.9, or the like. The NCBI accession number of the nucleotide sequence of cDNA of the human LAPTM5 gene is NM_006762.3. The NCBI accession number of the nucleotide sequence of cDNA of the human SLCO2B1 gene is NM_001145211.3, NM_001145212.3, NM_007256.5, or the like. The NCBI accession number of the nucleotide sequence of cDNA of the human LY86 gene is NM_004271.4.

In the production method of the present embodiment, examples of the pluripotent stem cell include an embryonic stem cell (an ES cell) and an induced pluripotent stem cell (an iPS cell). The pluripotent stem cell is preferably a human cell.

Examples of the transcription factor that increases the expression of the C3 gene include Spi-1 Proto-Oncogene (SPI1), CCAAT Enhancer Binding Protein Alpha (CEBPA), Platelet Activating Factor Receptor (PTAFR), Fli-1 Proto-Oncogene, ETS Transcription Factor (FLI1), Myocyte Enhancer Factor 2C (MEF2C), Early Growth Response 2 (EGR2), RUNX Family Transcription Factor 1 (RUNX1), Tumor Necrosis Factor (TNF), CCAAT Enhancer Binding Protein Beta (CEBPB), IKAROS Family Zinc Finger 1 (IKZF1), Kruppel Like Factor 6 (KLF6), Nuclear Factor I C (NFIC), E74 Like ETS Transcription Factor 4 (ELF4), Paired Box 8 (PAX8), PR/SET Domain 1 (PRDM1), Myocyte Enhancer Factor 2A (MEF2A), and Nuclear Receptor Subfamily 4 Group A Member 3 (NR4A3).

The NCBI accession number of the nucleotide sequence of cDNA of the human SPI1 gene is NM_001080547.2, NM_003120.3, or the like. The NCBI accession number of the nucleotide sequence of cDNA of the human CEBPA gene is NM_001285829.1, NM_001287424.2, NM_001287435.1, or the like. The NCBI accession number of the nucleotide sequence of cDNA of the human PTAFR gene is NM_000952.5, NM_001164721.2, NM_001164722.3, or the like. The NCBI accession number of the nucleotide sequence of cDNA of the human FLI1 gene is NM_001167681.3, NM_001271010.2, NM_001271012.2, or the like. The NCBI accession number of the nucleotide sequence of cDNA of the human MEF2C gene is NM_001131005.2, NM_001193347.1, NM_001193348.1, or the like. The NCBI accession number of the nucleotide sequence of cDNA of the human EGR2 gene is NM_000399.5, NM_001136177.3, NM_001136178.2, or the like. The NCBI accession number of the nucleotide sequence of cDNA of the human RUNX1 gene is NM_001001890.3, NM_001122607.2, NM_001754.5, or the like. The NCBI accession number of the nucleotide sequence of cDNA of the human TNF gene is NM_000594.4. The NCBI accession number of the nucleotide sequence of cDNA of the human CEBPB gene is NM_001285878.1, NM_001285879.1, NM_005194.4, or the like. The NCBI accession number of the nucleotide sequence of cDNA of the human IKZF1 gene is NM_001220765.3, NM_001220767.2, NM_001220768.2, or the like. The NCBI accession number of the nucleotide sequence of cDNA of the human KLF6 gene is NM_001160124.2, NM_001160125.2, NM_001300.6, or the like. The NCBI accession number of the nucleotide sequence of cDNA of the human NFIC gene is NM_001245002.2, NM_001245004.2, NM_001245005.2, or the like. The NCBI accession number of the nucleotide sequence of cDNA of the human ELF4 gene is NM_001127197.2, NM_001421.4, or the like. The NCBI accession number of the nucleotide sequence of cDNA of the human PAX8 gene is NM_003466.4, NM_013951.3, NM_013952.4, or the like. The NCBI accession number of the nucleotide sequence of cDNA of the human PRDM1 gene is NM_001198.4, NM_182907.3, or the like. The NCBI accession number of the nucleotide sequence of cDNA of the human MEF2A gene is NM_001130926.5, NM_001130927.5, NM_001130928.4, or the like. The NCBI accession number of the nucleotide sequence of cDNA of the human NR4A3 gene is NM_006981.4, NM_173199.4, or the like.

As will be described later in Examples, in a case of introducing nucleic acids containing open reading frames of these transcription factors into pluripotent stem cells, it is possible to induce differentiation into microglia. It is noted that the method of transfecting transcription factors into pluripotent stem cells to induce differentiation is also called forward programming. Nucleic acids containing open reading frames of these transcription factors may be used singly or in a combination of two or more thereof.

The nucleic acids containing open reading frames of these transcription factors may be mRNA or an expression vector. In addition, the expression vector may be a virus vector or may be a plasmid vector.

In the production method of the present embodiment, the transcription factor that increases the expression of the C3 gene preferably includes at least CEBPA, and it is preferably two or more transcription factors including at least CEBPA.

Examples of the more specific combination of transcription factors that increase the expression of the C3 gene include combinations of 2 to 5 transcription factors, which include CEBPA, CEBPB, KLF6, NFIC, or PAX8 among SPI1, CEBPA, PTAFR, FLI1, MEF2C, EGR2, RUNX1, TNF, CEBPB, IKZF1, KLF6, NFIC, ELF4, PAX8, PRDM1, MEF2A, NR4A3.

Examples of the still more specific combination of transcription factors that increase the expression of the C3 gene include a combination of CEBPA, MEF2C, and PAX8, a combination of CEBPA, CEBPB, and PAX8, a combination of CEBPA, NFIC, and PAX8, a combination of CEBPA and PAX8, a combination of CEBPB, KLF6, and PAX8, a combination of KLF6, NFIC, and PAX8, a combination of PTAFR, CEBPB, and PAX8, and a combination of CEBPA, KLF6, and PAX8.

As will be described later in Examples, in the production method of the present embodiment, the culture medium for culturing pluripotent stem cells introduced with a nucleic acid containing an open reading frame of a transcription factor is not particularly limited.

[Microglia]

In one embodiment, the present invention provides microglia produced by the production method described above. Due to being characterized by the production method, the microglia of the present embodiment are conceived to have a different gene expression profile and the like as compared with microglia obtained by inducing differentiation by other methods or microglia in vivo. However, it is very difficult and impractical to identify such a difference and identify whether or not it is the microglia of the present embodiment based on the difference in gene expression profile or the like. For this reason, it is realistic to carry out the identification by the production method.

EXAMPLES

Experimental Example 1

(Selection of Microglial Marker Gene)

With reference to published papers, a unique weighting was carried out to select a gene set capable of serving as microglia markers. Table 1 shows the set of microglial marker genes selected by the inventors of the present invention.

TABLE 1

| No. | Gene name |
|---|---|
| 1 | P2RY12 |
| 2 | C3 |
| 3 | CX3CR1 |
| 4 | CSF1R |
| 5 | A2M |
| 6 | ADAM28 |
| 7 | PLXDC2 |
| 8 | LAPTM5 |
| 9 | SLCO2B1 |
| 10 | LY86 |

Experimental Example 2

(Selection of Transcription Factors for Microglial Differentiation)

With reference to published papers, transcription factors for microglial differentiation were selected, where the transcription factors were conceived to be suitable for inducing differentiation into microglia. More specifically, transcription factors were selected, where the transcription factors were conceived to promote the expression of the microglial marker genes shown in Table 1 above in a case of being introduced into pluripotent stem cells. Table 2 below shows a list of transcription factors for microglial differentiation selected by the inventors of the present invention. For simplification, each gene is represented by one letter of the alphabet from “A” to “Q”.

TABLE 2

| Symbol | Name of transcription factor gene |
|---|---|
| A | SPI1 |
| B | CEBPA |
| C | PTAFR |
| D | FLI1 |
| E | MEF2C |
| F | EGR2 |
| G | RUNX1 |
| H | TNF |
| I | CEBPB |
| J | IKZF1 |
| K | KLF6 |
| L | NFIC |
| M | ELF4 |
| N | PAX8 |
| O | PRDM1 |
| P | MEF2A |
| Q | NR4A3 |

Experimental Example 3

(Primary Evaluation of Differentiation Induction)

Using the 17 kinds of transcription factors shown in Table 2, it was checked whether or not iPS cells could be induced to differentiate into microglia by forward programming of transfecting transcription factors into iPS cells. First, as a primary evaluation, the transcription factors shown in Table 2 above were transfected into iPS cells in 384 combinations shown in Table 3 below, and gene expression analysis was carried out.

TABLE 3

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | ABC | AEP | AIQ | BCG | BGQ | BLQ | CFP | CJO | DFQ | DKL | EHJ | ELO | FJL | GHO | HIJ | IOQ |
| 2 | ABD | AEQ | AJK | BCH | BHI | BMO | CFQ | CJP | DGJ | DKM | EHK | ELQ | FJN | GHP | HIK | IPQ |
| 3 | ABE | AFG | AJL | BCJ | BHJ | BMP | CGK | CKL | DGK | DKO | EHL | EMN | FJO | GHQ | HIL | JKM |
| 4 | ABF | AFI | AJM | BCK | BHK | BMQ | CGL | CKM | DGM | DKP | EHM | EMP | FJP | GIJ | HIQ | JKO |
| 5 | ABH | AFK | AJN | BDE | BHM | BNO | CGO | CKP | DGQ | DKQ | EHN | ENP | FJQ | GIK | HJK | JKQ |
| 6 | ABI | AFL | AJO | BDF | BHP | BNP | CGQ | CKQ | DHL | DLM | EHO | ENQ | FKL | GIM | HJL | JLO |
| 7 | ABK | AFN | AJP | BDG | BIK | BNQ | CHI | CLM | DHM | DLN | EHP | EOP | FKM | GIN | HJQ | JLP |
| 8 | ABQ | AGH | AJQ | BDH | BIL | BOP | CHK | CLN | DHN | DLO | EIJ | EPQ | FKN | GIP | HKM | JMP |
| 9 | ACD | AGK | AKM | BDN | BIM | BOQ | CHM | CLP | DHO | DLP | EIK | FGI | FKO | GIQ | HKO | JOP |
| 10 | ACE | AGL | AKN | BDP | BIN | BPQ | CHN | CMO | DHQ | DMQ | EIM | FGN | FKP | GJN | HKP | JPQ |
| 11 | ACF | AGM | AKO | BEF | BIP | CDE | CHO | CMP | DIJ | DNO | EIN | FGO | FLM | GJO | HLN | KLN |
| 12 | ACL | AGP | AKP | BEI | BJL | CDF | CHP | CNO | DIK | DNP | EIO | FGP | FLO | GJP | HLP | KLQ |
| 13 | ACM | AGQ | ALO | BEJ | BJM | CDG | CHQ | CNQ | DIL | DOP | EIP | FHI | FLQ | GKM | HLQ | KNQ |
| 14 | ACN | AHI | ALP | BEN | BJN | CDK | CIJ | COP | DIM | DPQ | EJM | FHJ | FMN | GKN | HMO | KOQ |
| 15 | ACQ | AHJ | AMN | BEO | BJO | CDN | CIL | COQ | DIN | EFG | EJN | FHM | FMO | GKP | HNI | LMN |
| 16 | ADE | AHK | AMO | BFG | BJQ | CDO | CIM | DEF | DIO | EFJ | EJQ | FHO | FMP | GKQ | HNQ | LMQ |
| 17 | ADF | AHL | AMP | BFH | BKL | CEG | CIN | DEG | DIP | EFL | EKL | FHP | FMQ | GLM | IJM | LOQ |
| 18 | ADJ | AHN | AMQ | BFK | BKN | CEI | CIO | DEH | DIQ | EFO | EKM | FHQ | FNP | GLN | IJN | MNO |
| 19 | ADL | AHO | ANO | BFM | BKO | CEJ | CIP | DEO | DJK | EFQ | EKN | FIJ | FOQ | GLO | IKL | MNP |
| 20 | ADM | AHP | ANQ | BGI | BKP | CEM | CIQ | DEP | DJL | EGH | EKO | FIK | FPQ | GLP | IKN | MNQ |
| 21 | ADO | AIL | AOQ | BGJ | BLM | CEQ | CJK | DEQ | DJM | EGJ | EKP | FIL | GHI | GLQ | ILP | MOP |
| 22 | AEF | AIN | BCD | BGL | BLN | CFG | CJL | DFG | DJN | EGL | EKQ | FIM | GHJ | GMN | IMQ | MOQ |
| 23 | AEG | AIO | BCE | BGM | BLO | CFL | CJM | DFH | DJP | EGM | ELM | FIO | GHM | GNO | INO | NOP |
| 24 | AEI | AIP | BCF | BGO | BLP | CFN | CJN | DFN | DJQ | EGO | ELN | FJK | GHN | GPQ | IOP | NPQ |

<<iPS Cell Culture>>

HPS1005 1383D2 (RIKEN BRC) was used as an iPS cell. StemFit AK02N (Ajinomoto Co., Inc., AJ100, hereinafter may be referred to as “StemFit”) was prepared according to the manufacturer’s instructions. CultureSure Y-27632 (FUJIFILM Wako Pure Chemical Corporation, 036-24023) was prepared to 10 mM with dimethylsulfoxide (DMSO). A coating solution was prepared by diluting iMatrix-511 silk (Takara Bio Inc., 892021) to 0.5 μg/cm$^2$ with phosphatebuffered saline (PBS) (−), and 20 mL of the coating solution was added to each of four 150 mm dishes and precoated at 37° C. for 1 hour.

After 1 hour, the coating solution was aspirated, Cells were seeded to $5.0\times10^5$ cells per dish using a culture solution obtained by adding a 1/1,000 volume of 10 mM CultureSure Y-27632 to StemFit (hereinafter, may be referred to as "Medium SY"), and the culture was carried out at 37° C. in 5% $CO_2$ until an appropriate cell number was reached. From the day after seeding, the culture medium was replaced using StemFit.

<<Seeding of iPS Cell>>

A 96-well plate was used for iPS cell culture. All wells of twelve 96-well plates were precoated with iMatrix-511 silk (Takara Bio Inc., 892021) at a concentration of 0.5 μg/cm$^2$, and aspiration was carried out immediately before seeding iPS cells.

The iPS cells cultured in a 150 mm dish were washed with PBS (−), a solution obtained by mixing equal volumes of TrypLE Select (1×) (Thermo Fisher Scientific, Inc., 12563-029) and 0.5 mmol/L-EDTA/PBS solution (Nacalai Tesque, Inc., 13567-84) was added incubated at 37° C. for 5 minutes, and then the cells were carefully stirred with a 1,000 μL micropipette to detach the cells from the dish and collected in a centrifuge tube.

The same amount of Medium SY as that of the cell suspension was added into the centrifuge tube, in which the cell suspension had been collected, to stop the TrypLE Select reaction. After centrifugation at 200×g for 3 minutes, the supernatant was aspirated to prepare a soft pellet, the pellet was loosened by tapping, and then Medium SY was added thereto to resuspend the cells.

Viability and cell number were measured by Countess (Thermo Fisher Scientific, Inc.), and cell suspensions having three concentration levels of $1.79\times10^5$ cells/mL, $3.04\times10^5$ cells/mL, and $4.30\times10^5$ cells/mL were prepared with Medium SY to prepare a confluency condition proper for transfection.

Aliquots of 100 μL of the cell suspension at each concentration were dispensed into the four coated 96-well plates to prepare four 96-well plates per concentration level for three concentration levels, and the culture was carried out at 37° C. in a 5% $CO_2$ environment.

<<Transfection>>

Transcription factors were transfected in the form of mRNA. The mRNA was thawed on ice and prepared to a concentration of 0.1 μg/μL, and four sets of mRNA mix stocks were prepared by mixing 0.5 μL with the combinations shown in Table 3 above to be 1.5 μL and kept frozen at −80° C. until the used in the transfection.

One day after iPS cell seeding (Day 1), four plates having a concentration level of 70% to 90% confluency were selected, the culture medium was replaced with StemFit, and the culture was carried out at 37° C. in a 5% $CO_2$ environment until transfection was carried out.

The temperature of Opti-MEM I Reduced Serum Medium (Thermo Fisher Scientific, Inc., 31985062, hereinafter may be referred to as "Opti-MEM") was returned to room temperature, and the mRNA mix stock was thawed on ice over 30 minutes.

A Mix 1 solution was prepared by mixing, per well of a 96-well plate, 1.5 μL of Lipofectamine Messenger MAX (Thermo Fisher Scientific, Inc., LMRNA001) in 36.7 μL of Opti-MEM and incubated at room temperature for 10 minutes. Next, a Mix 2 solution was prepared by adding 1.5 μL of the mRNA mix to 36.7 μL of Opti-MEM and carrying out mixing by tapping.

Subsequently, 12 μL of the Mix 2 solution was mixed with 12 μL of the incubated Mix 1 solution by pipetting to prepare a transfection solution, which was subsequently incubated for 5 minutes at room temperature. Subsequently, 20.8 μL of the transfection solution prepared according to the combination of mRNAs shown in Table 3 above was added dropwise to each well of the four 96-well plates seeded with iPS cells, and incubation was carried out for 3 hours at 37° C. in a 5% $CO_2$ environment. After 3 hours, the whole amount of StemFit was replaced, and incubation was carried out for 2 hours at 37° C. in a 5% $CO_2$ environment.

After 2 hours, the same transfection operation was carried out once again, incubation was carried out overnight at 37° C. in a 5% $CO_2$ environment, and two further times of transfection were carried out on Day 2, whereby transfection was carried out four times in total.

<<RNA-Seq Analysis for Primary Evaluation>>

On Day 3, all 384 wells of the four 96-well plates that had been subjected to the differentiation induction were subjected to RNA-seq. RNA-seq was carried out according to the Smart-seq2 method (Picelli S., et al., Full-length RNA-seq from single cells using Smart-seq2, Nat Protoc., 9 (1), 171-181, 2014.) and the Quartz-seq2 method (Sasagawa Y., et al., Quartz-Seq2: a high-throughput single-cell RNA-sequencing method that effectively uses limited sequence reads, Genome Biol., 19 (1), 29, 2018.).

Transcriptome data worthy of analysis were obtained from 354 samples obtained by the Smart-seq2 method and 297 samples obtained by the Quartz-seq2 method, collectively from 379 samples among the 384 samples.

From the obtained transcriptome data, TPM (Transcripts per million) in Smart-seq2 and CPM (Counts per million, a value obtained by normalizing the number of UMI counts by 1,000,000) in Quartz-seq2 were subjected to heat mapping with log 2, and the expression levels of seven genes of SLCO2B1, ADAM28, A2M, CSF1R, CX3CR1, C3, and P2RY12 were checked among the set of microglial marker genes shown in Table 1 above.

FIG. 1 is a heat map showing the expression state of microglial marker genes. In FIG. 1, the horizontal axis indicates the combination of transcription factors introduced into iPS cells, and the vertical axis indicates seven microglial marker genes. Here, the upper part shows a heat map of log 2 (CPM+1) of gene expression levels obtained by the Quartz-seq2 method, and the lower part shows a heat map of log 2 (TPM+1) of gene expression levels obtained by the Smart-seq2 method. The upper limit of the color scale is 6.

As a result of the analysis, according to the results of the Quartz-seq2 method, it was confirmed that C3 is expressed in almost all samples, followed by ADAM28 which is expressed in a large number of samples. In addition, from the results of the Smart-seq2 method, it was confirmed that although the observed TPM values are smaller than those of the Quartz-seq2 method, a large number of samples express C3. The above results suggested that iPS cells have differentiated into microglia-like cells in almost all combinations of transcription factors shown in Table 3 above.

Figure 2:
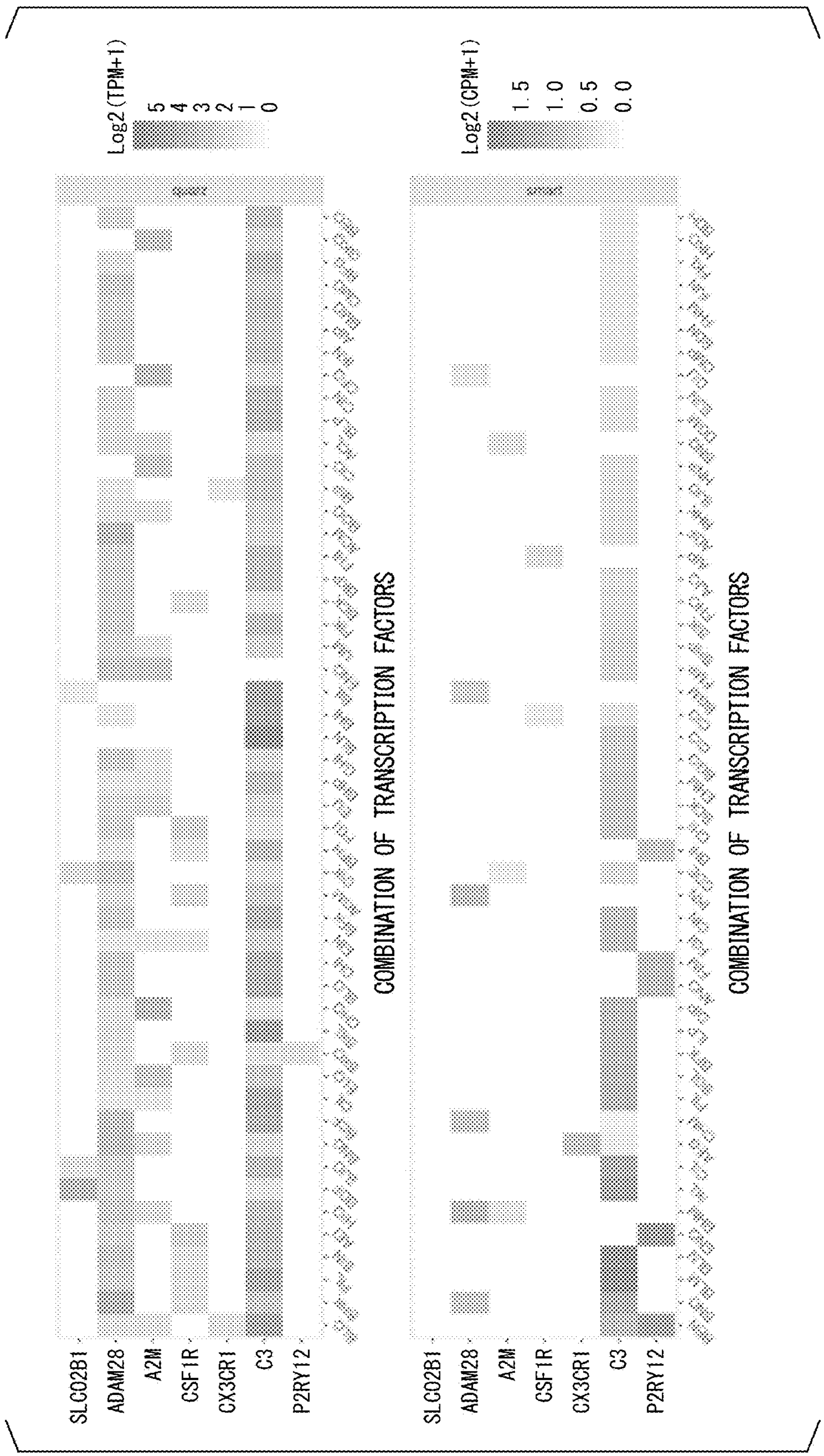
FIG. 2 is a heat map in which combinations of transcription factors introduced into iPS cells in Experimental Example 3 are arranged from the left in descending order of the expression levels of microglial marker genes.

FIG. 2 is a heat map in which combinations of transcription factors introduced into iPS cells are arranged from the left in descending order of the expression levels of the above seven genes. In FIG. 2, the horizontal axis indicates the combination of transcription factors, and the vertical axis indicates seven microglial marker genes. Here, the upper part shows a heat map of log 2 (CPM+1) of gene expression levels obtained by the Quartz-seq2 method (upper limit of color scale: 6), and the lower part shows a heat map of log 2 (TPM+1) of gene expression levels obtained by the Smart-seq2 method (upper limit of color scale: 2).

As a result of the analysis, it was confirmed that, among the 384 combinations, a combination containing transcription factors such as B, E, I, L, and N, in terms of transcription factor symbol, has high expression levels of microglial marker genes.

Subsequently, each of the transcriptome data, which had been obtained by the Smart-seq2 method and the Quartz-seq2 method, were subjected to principal component analysis and factor analysis. One figure showed the results of the principal component analysis of transcriptome data obtained by the Smart-seq2 method. In that figure, the horizontal axis indicated PC1, and the vertical axis indicated PC2. Another figure showed the results of the factor analysis of transcriptome data obtained by the Smart-seq2 method. The horizontal axis indicated Factor 1, and the vertical axis indicated Factor 2. The expression level of the microglial marker gene contributed to the positive direction of Factor 2.

As a result of the analysis, it was confirmed that combinations of transcription factors with high expression of microglial marker genes were distributed on the positive side of PC1 by the principal component analysis and the positive side of Factor 2 by the factor analysis.

Based on each of the results of the principal component analysis and the factor analysis by the Smart-seq2 method and the Quartz-seq2 method and based on the expression levels of the marker genes in FIG. 2, combinations of transcription factors more suitable for inducing differentiation into microglia were selected. Table 4 shows the selected combinations of transcription factors having a high ability to induce differentiation into microglia.

TABLE 4

| No. | Combination | No. | Combination |
|---|---|---|---|
| 1 | BI | 17 | BNQ |
| 2 | BN | 18 | CIN |
| 3 | BCF | 19 | DIJ |
| 4 | BDF | 20 | DIP |

TABLE 4-continued

| No. | Combination | No. | Combination |
|---|---|---|---|
| 5 | BDN | 21 | EIN |
| 6 | BEI | 22 | IKN |
| 7 | BEN | 23 | BKO |
| 8 | BFH | 24 | AOQ |
| 9 | BFK | 25 | GKN |
| 10 | BHP | 26 | ENQ |
| 11 | BIK | 27 | ABD |
| 12 | BIN | 28 | AEI |
| 13 | BKN | 29 | AGM |
| 14 | BKP | 30 | BIP |
| 15 | BLN | 31 | KLN |
| 16 | BNP | - | - |

Experimental Example 4

(Secondary Evaluation of Differentiation Induction)

Differentiation culture conditions were further investigated regarding the combination conditions of transcription factors. iPS cells were subjected to forward programming by transcription factor transfection with the combinations of transcription factors shown in Table 4, which had been determined to have a high ability to induce differentiation into microglia and were induced to differentiate with a culture medium for differentiation to induce differentiation into microglia, and the transcriptome analysis by RNA-seq was carried out.

<<Culture Medium for Differentiation>>

A combination of transcription factors was transfected into iPS cells, which were subsequently induced to differentiate into microglia for 4 days in a culture medium for differentiation. As culture media for differentiation, the following three kinds of basal media were used: Neurobasal Media, DMEM/F-12, and Advanced DMEM/F-12. IL-34, M-CSF, GlutaMAX, and Component P were added to each of the basal media to obtain culture media designated as M1, M2, and M3. In addition, CD200, CX3CL1, and TGF-beta were added to M1, M2, and M3 to obtain culture media each designated as M4, M5, and M6. Table 5 below shows the compositions of the six kinds of the culture media M1 to M6.

TABLE 5

| Contents | Vendor | Final Conc. | M1 | M4 | M2 | M5 | M3 | M6 |
|---|---|---|---|---|---|---|---|---|
| Neurobasal Medium | Thermo Fisher Scientific, Inc. | — | 1 | 1 | 0 | 0 | 0 | 0 |
| DMEM/F12 | Thermo Fisher Scientific, Inc. | — | 0 | 0 | 1 | 1 | 0 | 0 |
| Advanced DMEM/F12 | Thermo Fisher Scientific, Inc. | — | 0 | 0 | 0 | 0 | 1 | 1 |
| N2 Supplement (100X) | Thermo Fisher Scientific, Inc. | 1% | 1 | 1 | 1 | 1 | 1 | 1 |
| IL-34 | PeproTech, Inc. | 0.1 μg/mL | 1 | 1 | 1 | 1 | 1 | 1 |
| M-CSF | PeproTech, Inc. | 0.025 μg/mL | 1 | 1 | 1 | 1 | 1 | 1 |
| GlutaMAX | Thermo Fisher Scientific, Inc. | 1% | 1 | 1 | 1 | 1 | 1 | 1 |
| Component P | Elixirgen Scientific, Inc. | 0.1% | 1 | 1 | 1 | 1 | 1 | 1 |
| Recombinant Human CD200 | R&D Systems Inc. | 0.1 μg/mL | 0 | 1 | 0 | 1 | 0 | 1 |
| CX3CL1 | PeproTech, Inc. | 0.1 μg/mL | 0 | 1 | 0 | 1 | 0 | 1 |
| TGF-beta | PeproTech, Inc. | 0.05 μg/mL | 0 | 1 | 0 | 1 | 0 | 1 |
| NaCl 5M | Sigma-Aldrich Co. LLC | 50 mM | 1 | 1 | 0 | 0 | 0 | 0 |
| lactic acid (85% syrup stock) | Sigma-Aldrich Co. LLC | 0.017% | 1 | 1 | 0 | 0 | 0 | 0 |
| Sodium Pyruvate (100 mM) | Thermo Fisher Scientific, Inc. | 1 mM | 1 | 1 | 0 | 0 | 0 | 0 |
| Biotin | FUJIFILM Wako Pure Chemical Corporation | 3.5 ng/ml | 1 | 1 | 0 | 0 | 0 | 0 |

TABLE 5-continued

| Contents | Vendor | Final Conc. | M1 | M4 | M2 | M5 | M3 | M6 |
|---|---|---|---|---|---|---|---|---|
| lipidated BSA (Albumax I) | Thermo Fisher Scientific, Inc. | 2 mg/mL | 1 | 1 | 0 | 0 | 0 | 0 |
| Penicillin-Streptomycin | Nacalai Tesque, Inc. | 1% | 1 | 1 | 1 | 1 | 1 | 1 |
| Ascorbic Acid | Sigma-Aldrich Co. LLC | 2.5 μg/mL | 0 | 0 | 1 | 1 | 0 | 0 |
| NEAA | Thermo Fisher Scientific, Inc. | 1% | 0 | 0 | 1 | 1 | 0 | 0 |

<<Differentiation Culture>>

Until transfection, differentiation culture was carried out in triplicate with respect to the six different culture media for differentiation under the 32 conditions of the 31 kinds of combinations of transcription factors shown in Table 4 above and ntfc (no transcription factor control) with culture medium for differentiation alone for checking the differentiation induction, where Nuclease-free Water was used instead of the mRNA mix in the ntfc.

Transfection was carried out according to the same protocol as in Experimental Example 3. A combination of two kinds of transcription factors of 0.75 μL was mixed at a concentration of 0.1 μg/μL to obtain 1.5 μL of an mRNA mix. In addition, in order to investigate a case of transfection with only one kind of transcription factor, 1.5 μL of the mRNA in Table 2 above was transfected at a concentration of 0.1 μg/μL. siPOU5F1 (Thermo Fisher Scientific, Inc., s10873) was added at 20 nM at the time of the preparation of all the first transfection solutions.

At the time of the culture medium replacement after the fourth transfection on Day 2, the culture medium was changed from StemFit to the culture medium for differentiation shown in Table 5 above. The culture medium for differentiation was replaced every other day, and all samples were subjected to RNA extraction on Day 7.

Samples transfected with only one kind of transcription factor were subjected to culture medium exchange to StemFit and then subjected to RNA extraction on Day 3.

Subsequently, RNA-seq was carried out by the Quartz-seq2 method. In addition, at the time of RNA-seq, total RNA extracted after the culture and total RNA extracted from the iPS cells collected at the time of seeding were used, and the following cells were used as controls: Human Microglia Primary Cell Culture Total RNA: 50 μg (Celprogen, 37089 RNA), Total RNA Human Monocytes, 1 μg (3H Biomedical, 3H100-30-10), Total RNA Human Dendritic Cells (MoDCs), 1 μg (3H Biomedical, 3H100-70-10), and Human Macrophage Primary Cell Culture-Frozen Vial (Celprogen, 36070-01). RNeasy mini kit (Qiagen, 74004) was used for the extraction of total RNA.

<<RNA-seq Analysis for Secondary Evaluation>>

Figure 3:
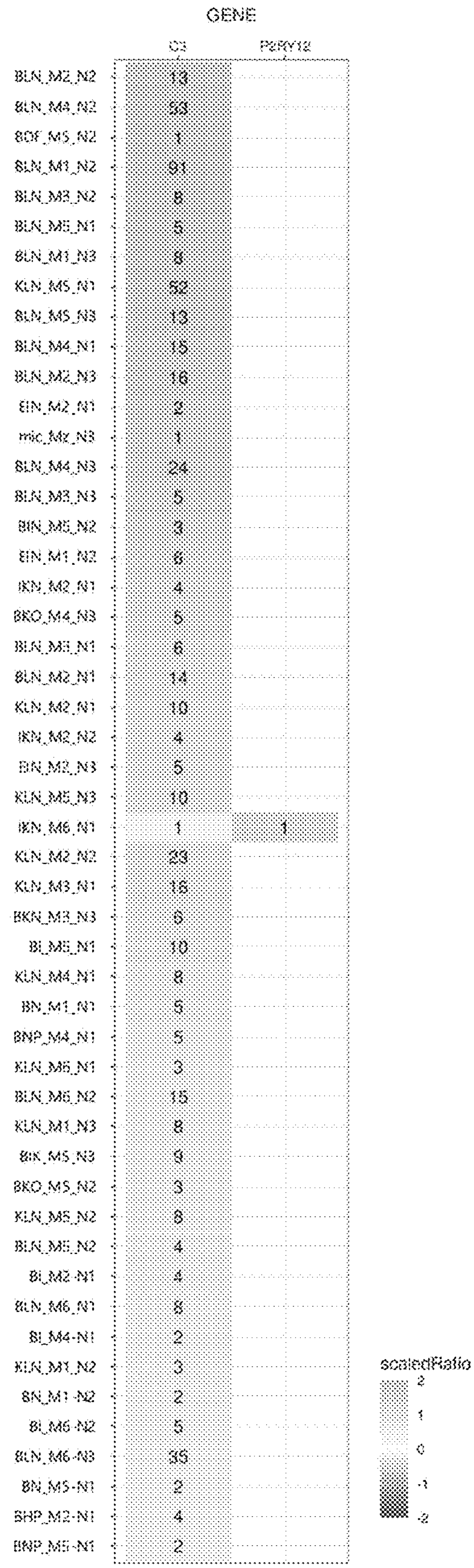
FIG. 3 is a view summarizing results of an RNA-seq analysis in Experimental Example 4.

The expression levels of C3 and P2RY12 were checked regarding the UMI counts obtained by the Quartz-seq2 method. FIG. 3 is a view summarizing the results of RNA-seq analysis. In FIG. 3, the numbers in the cells indicate the UMI counts. Here, the top 50 samples arranged in descending order of expression levels of C3 and P2RY12 are shown after normalizing the variation in the UMI counts between samples by 1,000,000. In addition, the microglial control is positioned at the 13th raw. No expression of P2RY12 was confirmed in the microglia control.

In addition, in the iPS cells introduced with a combination of transcription factors including B, I, K, L, and N, such as BLN, KLN, or IKN, C3 was highly expressed, and BLN was included in the top 50 samples regardless of the kind of culture medium for differentiation.

Figure 4:
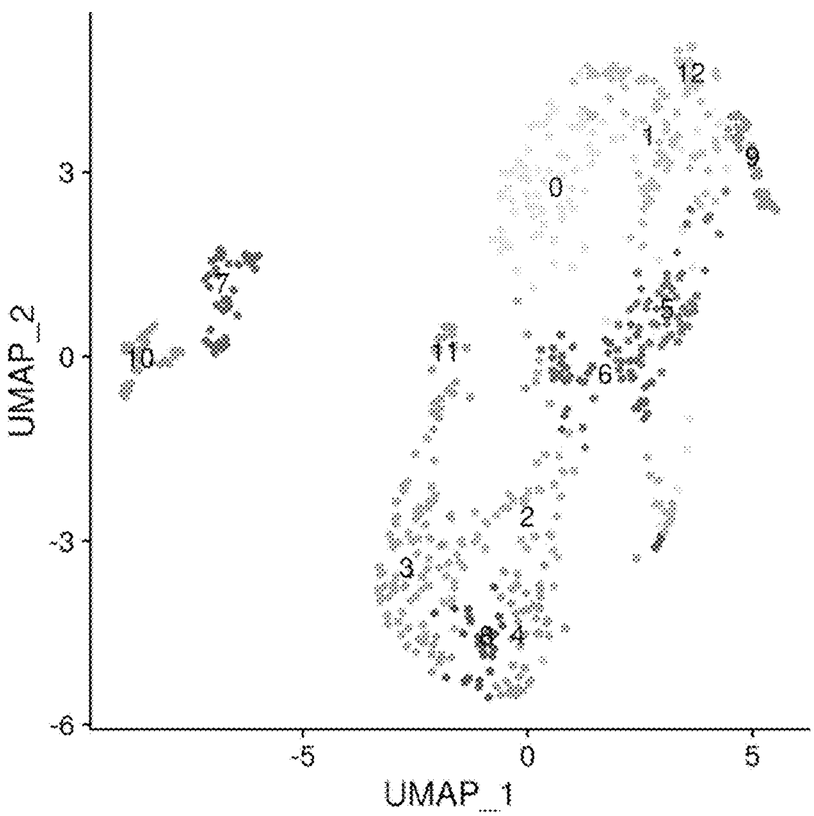
FIG. 4 is a view showing results of carrying out clustering by UMAP in Experimental Example 4.

FIG. 4 is a view showing the results of carrying out clustering by UMAP. As a result of the analysis, 13 clusters were confirmed. We classified UMAP clustering for M0 which is a sample subjected to RNA extraction on Day 3 after the introduction of only one kind of transcription factor, culture media for differentiation M1 to M6, and Mz which is various controls.

As a result of the classification, it was revealed that clusters 9 and 12 in FIG. 4 are samples in which only one kind of transcription factor has been introduced and RNA has been extracted on Day 3. Regarding the control, it was revealed that microglia are distributed in the cluster 1, and monocytes, dendritic cells, and macrophages are distributed in the cluster 10.

When the culture media for differentiation were compared, the clusters 7 and 10 were absent in Neurobasal-based M1 and M4. This suggested that samples induced to differentiate in a Neurobasal-based manner would not be in a transcriptome state similar to that of monocytes, dendritic cells, or macrophages.

When the samples distributed at positions close to the control of microglia were checked, BIN, CIN, BN, and BKN were frequently distributed.

In addition, the samples distributed close to monocytes, dendritic cells, and macrophages were ABD, AEI, BDF, DIJ, and DIP.

From the above results, the secondary evaluation using the culture media for differentiation revealed that a suitable method of carrying out differentiation into microglia is selecting a combination including B, I, K, L, and N, such as BLN, KLN, or IKN, from the transcription factor candidates in Table 2 above.

Experimental Example 5

(Function Evaluation)

It was checked whether the phagocytic activity, which is a function of microglia, was exhibited in the combinations of transcription factors that were suggested to have a high microglia differentiation potential in the secondary evaluation.

<<Differentiation Induction Condition>

Based on the results of the primary evaluation and the secondary evaluation, the induction of iPS cell differentiation into microglia with a combination of transcription factors BN, BEN, BIN, BLN, IKN, or KLN was evaluated. In addition, for comparison, a combination of transcription factors, AB, ABD, AEI, DIJ, or DIP, which provided a transcriptome state similar to that of the control hematopoietic cells, was also used to induce differentiation.

The differentiation induction conditions of Experimental Example 4 were scaled up to those for a 24-well plate, and the differentiation induction was carried out at N4 with each combination of transcription factors. M6 was used as the culture medium for differentiation. Similar to Experimental Example 4, differentiation was induced in the culture medium for differentiation M6 after four transfections. Subsequently, RNA was extracted from samples for N3 on Day 7 using the RNeasy mini kit, and RNA-seq was carried out by the Smart-seq2 method.

In addition, iCell microglia (FUJIFILM Wako Pure Chemical Corporation, C1110), in addition to the iPS cells at the time of seeding, the ntfc, and the microglia, the monocytes, and the dendritic cells the same as those used in Experimental Example 4, were cultured, and each total RNA was extracted as a control with the RNeasy mini kit. The remaining N1 was continuously cultured in the culture medium for differentiation M6 from Day 7, subcultured on Day 11, and cultured in the M6 culture medium to which Component P was not added. Subsequently, a time-lapse movie of 13 hours was taken overnight on Day 14 to check the phagocytic activity of the differentiated cells.

<<RNA-seq by Smart-seq2 Method>>

At the time of the RNA extraction on Day 7, adherent cells were few in AB, ABD, AEI, DIJ, and DIP, and ntfc. Therefore, floating cells were centrifuged to precipitate the cells and subjected together with the adherent cells to RNA extraction.

In the cDNA quality check by the Smart-seq2 method, it was confirmed that in the described above combinations of transcription factors and the microglial control (Celprogen), the chain length of cDNA is short, and thus the RNA quality is poor.

Among the microglia markers shown in Table 1 above, the expression levels of the following genes were confirmed: C3 and P2RY12, which are conceived to be important markers, in addition to APOE, BHLHE41, CABLES1, OLFML3, PROS1, SLC7A8, SLCO2B1, TMEM119, and TREM2, which have been confirmed as genes specifically expressed microglia.

Figure 5:
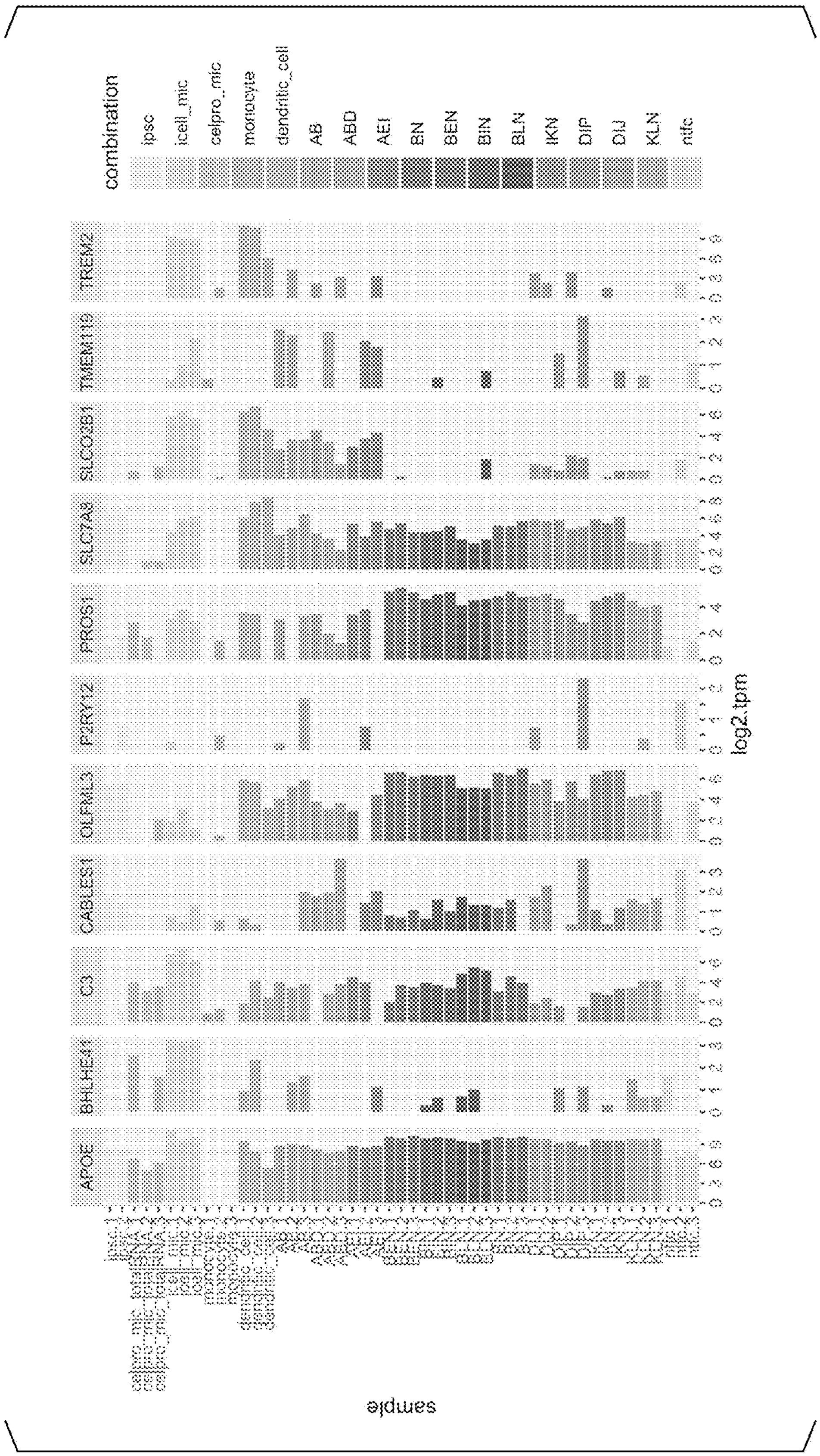
FIG. 5 is a view showing expression levels of respective microglia marker genes in Experimental Example 5.

FIG. 5 is a view showing expression levels of the respective microglia marker genes. In FIG. 5, the horizontal axis indicates the expression level. As a result, the expression of almost all marker genes was confirmed in the iCell microglia. P2RY12, which is conceived to be an important marker, was slightly expressed even in the iCell microglia, and AB, AEI, DIJ, DIP, and KLN were confirmed in the differentiation-induced samples only for N1.

C3 was highly expressed in the microglia (Celprogen) and the iCell microglia. In addition, the combination of BN, BEN, BIN, BLN, IKN, or KLN, which was suggested to have a high ability to induce differentiation into microglia in Experimental Examples 3 and 4, reproduced a high expression level.

Further, in the microglial markers shown in FIG. 5, it was confirmed that the total level of expression levels is high in the combination of BN, BEN, BIN, BLN, IKN, KLN, or DIP.

<<Function Evaluation>>

At the time of subculture on Day 11, adherent cells were few in AB, ABD, AEI, DIJ, DIP, and ntfc, and thus the subculture was carried out only on BEN, BIN, BLN, BN, IKN, and KLN. On Day 14, time-lapse imaging was carried out overnight for 13 hours using CQ1 (Yokogawa Electric Corporation).

Figure 6:
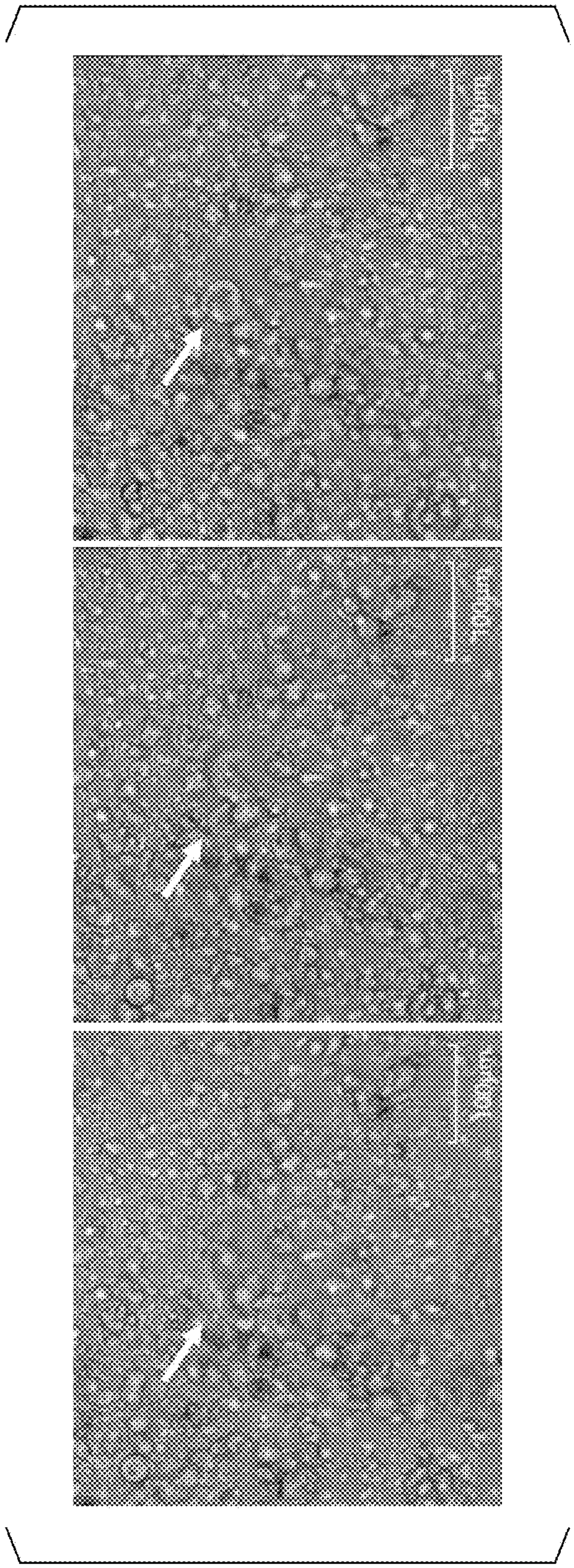
FIG. 6 is microscopic images showing a part of a time-lapse movie of a representative phagocytosis scene of microglia in Experimental Example 5.
Figure 7:
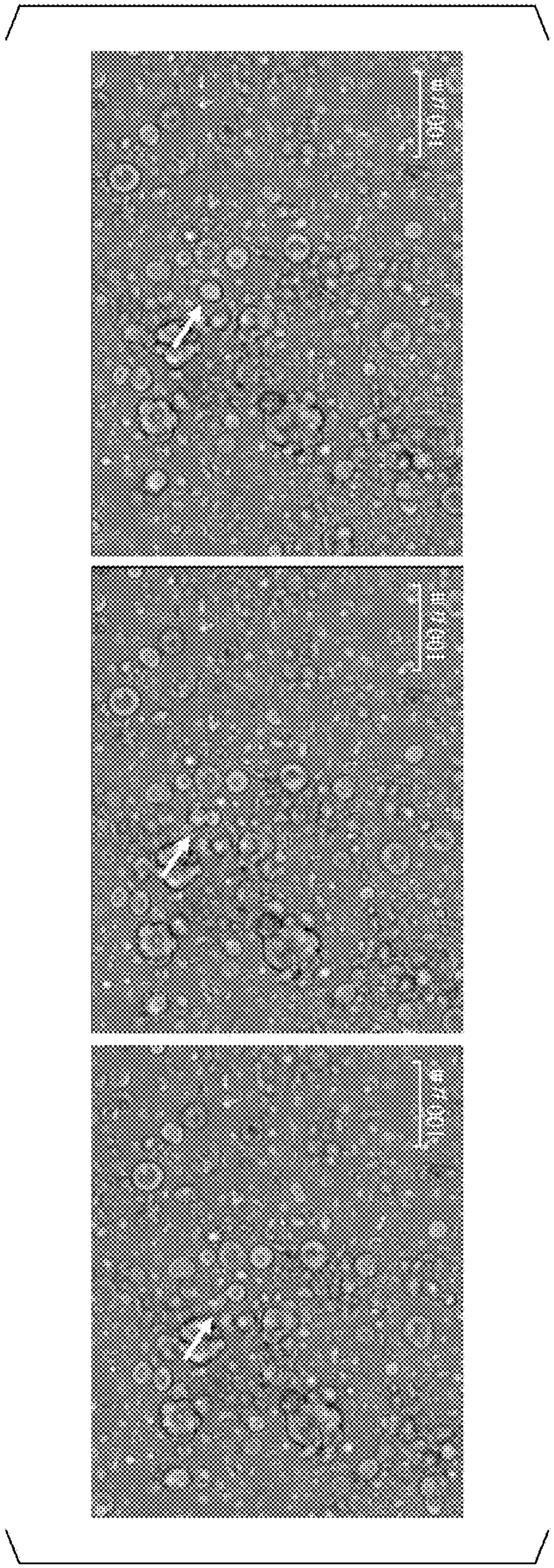
FIG. 7 is microscopic images showing a part of a time-lapse movie of a representative phagocytosis scene of microglia in Experimental Example 5.

FIG. 6 shows a representative phagocytosis scene in the time-lapse movie of BN, and FIG. 7 shows a representative phagocytosis scene of BLN. In FIG. 6 and FIG. 7, time elapses from left to right. In addition, arrows indicate phagocytic cells having phagocytic activity. As a result, the cells having phagocytic activity actively migrated, had relatively large cell sizes of about 30 μm to 100 μm, and phagocytosed cells one after another. BEN, BIN, BLN, BN, IKN, and KLN, which could be subcultured, were confirmed to have phagocytic activity in the time-lapse movie.

From the above results, it was confirmed that iPS cells can be induced to differentiate into microglia in 14 days by transfecting a combination of transcription factors that increase the expression of C3 and other microglia-specific marker genes.

The present invention includes the following aspects.

[1] A production method for microglia, including a step of introducing, into pluripotent stem cells, a nucleic acid including an open reading frame of a transcription factor that increases expression of a Complement C3 (C3) gene.

[2] The production method according to [1], in which the transcription factor is selected from the group consisting of SPI1, CEBPA, PTAFR, FLI1, MEF2C, EGR2, RUNX1, TNF, CEBPB, IKZF1, KLF6, NFIC, ELF4, PAX8, PRDM1, MEF2A, and NR4A3.

[3] The production method according to [2], in which the transcription factor includes at least CEBPA.

[4] The production method according to [2] or [3], in which the transcription factor is two or more transcription factors including at least CEBPA.

CITATION LIST

Patent Documents

[Patent Document 1] PCT International Publication No. WO2020/252477

[Patent Document 2] United States Patent Application, Publication No. 2020/0063105

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

What is claimed is:

1. A method of producing microglia, comprising: introducing, into pluripotent stem cells, a nucleic acid including an open reading frame of a combination of transcription factors that increases expression of a Complement C3 (C3) gene, wherein the combination of transcription factors is selected from the group consisting of BIN, CIN, BN, BKN, BEN, BLN, IKN and KLN, wherein B is CEBPA, C is PTAFR, E is MEF2C, I is CEBPB, K is KLF6, L is NFIC, and N is PAX8.

2. The method according to claim 1, wherein the combination of transcription factors includes at least CEBPA.

* * * * *